(12) United States Patent
Yamada

(10) Patent No.: US 7,559,229 B2
(45) Date of Patent: Jul. 14, 2009

(54) GAS SENSOR WITH INCREASED WATER-INCURSION RESISTANCE AND METHOD OF OPERATING GAS SENSOR

(75) Inventor: Kouhei Yamada, Oobu (JP)

(73) Assignee: Denso Corporation, Kariya (JP)

(*) Notice: Subject to any disclaimer, the term of this patent is extended or adjusted under 35 U.S.C. 154(b) by 33 days.

(21) Appl. No.: 11/806,899

(22) Filed: Jun. 5, 2007

(65) Prior Publication Data

US 2008/0016948 A1 Jan. 24, 2008

(30) Foreign Application Priority Data

Jul. 21, 2006 (JP) .............................. 2006-199073
Dec. 15, 2006 (JP) .............................. 2006-337819

(51) Int. Cl.
*G01N 9/00* (2006.01)
(52) U.S. Cl. ....................................... 73/31.05; 73/23.2
(58) Field of Classification Search ................. 73/31.05; 204/428
See application file for complete search history.

(56) References Cited

U.S. PATENT DOCUMENTS

| 6,279,376 | B1 * | 8/2001 | Yamada et al. ............... 73/23.2 |
| 6,319,378 | B1 * | 11/2001 | Kojima et al. ............... 204/427 |
| 6,945,091 | B2 * | 9/2005 | Nakagawa ................... 73/31.05 |
| 7,007,543 | B2 * | 3/2006 | Sakawa et al. ............ 73/23.32 |
| 7,124,623 | B2 * | 10/2006 | Nakagawa ................... 73/23.31 |
| 7,159,447 | B2 * | 1/2007 | Nakagawa ................... 73/31.05 |
| 2004/0129069 | A1 * | 7/2004 | Sakawa et al. ............ 73/118.1 |
| 2004/0144645 | A1 * | 7/2004 | Yamada et al. ............... 204/424 |
| 2005/0178187 | A1 * | 8/2005 | Nakagawa ................... 73/31.05 |

FOREIGN PATENT DOCUMENTS

| JP | 2003-194767 | 7/2003 |
| JP | 2004-245103 | 9/2004 |

* cited by examiner

*Primary Examiner*—Hezron Williams
*Assistant Examiner*—Mark Shabman
(74) *Attorney, Agent, or Firm*—Nixon & Vanderhye, PC

(57) ABSTRACT

A gas sensor and a related method operating are disclosed as having a concentration sensing element for detecting a concentration of a specified gas component in the measuring gases. A housing supports the concentration sensing element and a cover body structure, which includes an inner shell and an outer shell for surrounding a leading end portion of the concentration sensing element in an area exposed to a measuring gas flow passage. An annular sideways clearance is defined between the inner shell and the outer shell. The inner shell has a sidewall whose upper area is formed with inner-shell sidewall openings and a bottom wall formed with an inner-shell bottom wall opening. The outer shell has a sidewall formed with outer-shell sidewall openings and a bottom wall having outer-shell bottom wall openings formed in an outer circumferential area radially outside the inner-shell bottom wall opening.

14 Claims, 11 Drawing Sheets

GAS SENSOR WITH INCREASED WATER-INCURSION RESISTANCE AND METHOD OF OPERATING GAS SENSOR

CROSS REFERENCE TO RELATED APPLICATIONS

This application is related to Japanese Patent Application Nos. 2006-199073 and 2006-337819, filed on Jul. 21, 2006 and Dec. 15, 2006, respectively, the contents of which are hereby incorporated by reference.

BACKGROUND OF THE INVENTION

1. Technical Field of the Invention

The present invention relates to gas sensors for detecting a concentration of a specified gas component in measuring gases of, for instance, automotive engines or the like and, more particularly, to a gas sensor having a cover body structure for protecting a gas sensing element.

2. Description of the Related Art

With the development of automotive engines, attempts have heretofore been made to provide a gas sensor mounted on an exhaust pipe of an internal combustion engine such as an automotive engine. The gas sensor detects a concentration of, for instance, a specified gas component such as oxygen in measuring gases to output a detection signal. The detection signal is applied to an electronic control unit, which calculates an air-fuel ratio based on the detected oxygen concentration for thereby performing combustion control of the internal combustion engine.

With such a structure, the gas sensor generally includes a housing fixedly installed on a wall of an exhaust gas flow passage, a gas sensing element inserted through the housing and held in a fixed place with a leading end portion exposed to the exhaust gas flow passage, and a cover body structure covering the leading end portion of the gas sensing element to protect the same from exhaust gases.

Meanwhile, during a startup operation of the internal combustion engine at a low temperature, the exhaust pipe remaining under a cold condition absorbs a heat of moisture, contained in exhaust gases, which in turn is condensed to form water droplets. The water droplets travel through the exhaust gas flow passage. Then, no evaporation of the water droplets takes place and the water droplets intrude an inside of the gas sensor together with measuring gases. Thus, the water droplets tend to adhere onto the gas sensing element with a resultant adverse affect as described below.

In general practice, the gas sensing element, made of a solid electrolyte or the like, is heated with a heater or the like to a high temperature greater than 400° C. to be maintained in an activated state.

Therefore, as the water droplets enters the inside of the gas sensor and adhere onto the gas sensing element, there is a fear of the gas sensing element subjected to a thermal impact to cause a cracking to take place due to water-incursion.

Further, with a view to performing combustion control of the internal combustion engine with increased precision, there is a need for the gas sensor to have a further increased response. Therefore, for the gas sensor to have the increased response, the gas sensor needs to have a structure to immediately admit measuring gases to the inside of the gas sensor.

Accordingly, the cover body of the gas sensor is required to have antimony characteristics with water-incursion resistance and high response.

To satisfy such requirement, attempt has heretofore been made to provide a gas sensor including a cover body formed in a double-layered cylindrical structure composed of an inner shell and an outer shell that are different in diameter from each other as disclosed in Japanese Patent Application Publication 2004-245103. With such a cover body, the inner shell and the outer shell have gas induction holes, respectively, for admitting measuring gases to an inside of the gas sensor so as to ensure a response. The cover body has a sideways clearance defined in a fixed range between an outer periphery of the inner shell and an inner wall of the outer shell, thereby attempting to prevent water droplets from intruding from the sided area of the cover body so as to minimize the occurrence of water-incursion.

In addition, an outer-shell bottom wall opening, formed on an outer-shell bottom wall, and an inner-shell bottom wall opening, formed on an inner-shell bottom wall, are located in a concentric relation to each other, with the inner-shell bottom wall opening being directly exposed to the exhaust gas stream passing through the exhaust gas flow passage.

Further, the present inventors have proposed a gas sensor including a cover body formed in a structure to provide increased water-incursion resistance as disclosed in Japanese Patent Application Ser. No. 2006-124074. An example of a gas sensor with such a structure is shown in FIG. 12.

In FIG. 12, the gas sensor 1C includes a gas sensing element 11 and a cover body formed in a double-layered cylinder structure.

The cover body includes an inner shell 12C and an outer shell 13C, with the outer shell 13C having outer-shell sidewall openings 132C while the inner shell 12C has inner-shell sidewall openings 123C formed in an area axial far from the outer-shell sidewall openings 132C in a direction closer to an inner-shell bottom wall. In addition the outer shell 13C and the inner shell 12C have bottom wall openings 133C and 126C, respectively, formed in a concentric position.

The inner-shell sidewall openings 123C are formed so as to open upward in a direction from an external area of the inner shell 12C to an inside thereof in an upward component. This prevents the water droplets, incoming with the exhaust gas stream through the outer-shell sidewall openings 132C, from entering the inside of the inner shell 12C.

The water droplets in exhaust gases move downward along an inner wall of a reduced diameter portion 124C, formed on the inner shell 12C at a leading end portion thereof, upon which the water droplets are expelled through the bottom wall openings 133C to the measuring gas flow passage.

The bottom wall opening 126C, formed on a bottom wall 125C of the inner shell 12C, is placed on the same plane as the bottom wall opening 133C formed on a bottom wall 135C of the outer shell 13C or a position protruding downward from the bottom wall opening 133C to be directly exposed the measuring gas flow passage.

However, with the structure of the gas sensor disclosed in the related art mentioned above and the structure of the gas sensor shown in FIG. 12, the bottom wall opening, formed on the bottom wall of the inner shell, is exposed to the exhaust gas flow passage, it becomes hard for the gas sensor to completely prevent the water droplets, contained in exhaust gases, from intruding through the inner-shell bottom wall opening depending on an angle at which the gas sensor is mounted on the wall of the exhaust pipe. Especially, under a circumstance where the bottom wall opening 126C, formed on the bottom wall 125C of the inner shell 12C, is placed on the same plane as the bottom wall opening 133C formed on the bottom wall 135C of the outer shell 13C, not only the water droplets, contained in exhaust gases, directly intrude the inside of the inner shell 12C but also the water droplets, remaining on an opening edge of the outer-shell bottom wall opening 133C, are caused to scatter when an exhaust gas stream flows at a high velocity. Thus, there is a fear of the water droplets intruding the inside of the inner shell 12C to adhere onto the gas sensing element.

SUMMARY OF THE INVENTION

The present invention has been completed with a view to addressing the above issues and has an object to provide a gas sensor formed in a structure that enables a gas sensing element to be less susceptible to water-incursion while enhancing an excellent response.

To achieve the above object, a first aspect of the present invention provides a gas sensor for detecting a concentration of a specified gas component in measuring gases, comprising a concentration sensing element having a base end portion and a leading end portion for detecting the concentration of the specified gas component in the measuring gases, a housing for insertion of the concentration sensing element to fixedly support the concentration sensing element to allow the leading end portion of the concentration sensing element in a flow passage through which a stream of measuring gases flows, and a bottomed cylindrical cover body structure, fixedly supported with the housing and having a cylindrical multiple-layer structure, which includes an inner shell and an outer shell different in diameter from each other and disposed in a concentric relation to each other so as to surround the leading end portion of the concentration sensing element in an area exposed to the stream of measuring gases. An annular sideways clearance is defined between an outer periphery of the inner shell and an inner periphery of the outer shell. The inner shell has a base end portion and a leading end portion, the base end portion of the inner shell having inner-shell sidewall openings formed in components directed upward from an outside area of the inner shell to an inside area thereof, the inner shell having an inner-shell bottom wall whose central area is formed with an inner-shell bottom wall opening. The outer shell has a base end portion and a leading end portion, the base end portion of the outer shell having a plurality of outer-shell sidewall openings for admitting the stream of measuring gases to the annular sideways clearance. The leading end portion of the outer shell has an outer-shell bottom wall spaced from the inner-shell bottom wall to define a bottom clearance therebetween. A plurality of outer-shell bottom wall openings are formed on the outer-shell bottom wall in an outer circumferential area radially outside the inner-shell bottom wall opening.

In general, a measuring gas stream is admitted through the outer-shell sidewall openings to the sideways clearance defined between an outer periphery of the inner shell and an inner periphery of the outer shell, thereby forming a stream in a direction toward the outer-shell bottom wall openings. Due to a particular structure of the inner shell with the inner-shell sidewall openings oriented upward with respect to the inner wall of the inner shell, no water droplet is admitted to the inner-shell sidewall openings even in the presence of water droplets in the measuring gas stream while only measuring gases are admitted to the inside of the inner shell through the inner-shell sidewall openings. Accordingly, the water droplets admitted through the outer-shell sidewall openings are immediately expelled through the outer-shell bottom wall openings to the measuring gas flow passage. Thus, the concentration sensing element is less susceptible to water-incursion.

Further, no direct fluid communication is established between the inner-shell bottom opening and the outer-shell bottom wall openings. Therefore, no water droplet directly intrudes the inside of the inner shell even when the water droplets intrude through the outer-shell bottom wall openings and the water droplets passing through the bottom clearance between the inner-shell bottom wall and the outer-shell bottom wall are caused to evaporate to be diminished. Thus, the concentration sensing element is made less susceptible to water-incursion with the resultant increase in response of the gas sensor.

With the gas sensor of the present embodiment, the leading end portion of the inner shell may preferably include a tapered portion that decreases in diameter toward the inner-shell bottom wall.

With such a structure of the inner shell, the sideways clearance defined between the inner wall of the outer shell and the outer periphery of the inner shell is expanded in space toward the outer-shell bottom wall. This results in a drop in pressure loss of the sideways clearance. Therefore, the measuring gas stream, admitted to the sideways clearance through the outer-shell sidewall openings, immediately move, making it easy for the water droplet, contained in the measuring gas stream, to be expelled through the outer-shell bottom wall openings to the outside of the gas sensor. Accordingly, the concentration sensing element is further less susceptible to water-incursion.

In addition, the inner shell has a reduced inner volume to achieve a quickened exchange of measuring gases, thereby providing an increase in a response of the gas sensor.

With the gas sensor of the present embodiment, the inner shell may preferably include a tapered shoulder, formed in an area between the base end portion and the leading end portion of the inner shell, which decreases in diameter toward the inner-shell bottom wall, and a plurality of concaved portions, formed in the area between the base end portion and the leading end portion of the inner shell, wherein the inner-shell sidewall openings are formed in slit shapes in at least one of the tapered shoulder and the plurality of concaved portions.

With the inner-shell sidewall openings formed in the slit shapes opening toward an upper and inward area of the base end portion of the inner shell, the water droplets becomes hard to intrude into the inside of the inner shell. Thus, the concentration sensing element is less susceptible to water-incursion.

With the gas sensor of the present embodiment, the leading end portion of the outer shell may preferably include a tapered portion that decreases in diameter toward the outer-shell bottom wall.

With such a structure, the sideways clearance between an inner wall of the tapered portion of the outer shell and an outer wall of the inner shell is partially narrowed. This causes a stream of measuring gases, admitted to the inside of the outer shell, to flow toward the outer-shell bottom wall at an accelerated speed. Therefore, the water droplets, admitted through the outer-shell sidewall openings, are liable to be expelled from the outer-shell bottom wall openings. Accordingly, the concentration sensing element is less susceptible to water-incursion.

With the gas sensor of the present embodiment, the plurality of outer-shell bottom wall openings may preferably include three to six openings formed at equidistantly spaced positions in a circular area concentric to an axis of the outer shell.

With the outer-shell sidewall formed with such number of outer-shell bottom wall openings, the gas sensor can have optimum response with increased water-incursion resistance.

If the number of outer-shell bottom wall openings is less than 2, then, a need arises to install the gas sensor on the exhaust gas pipe upon specifying directivity on installation, resulting in practical disadvantage. In addition, the introduction and expelling of measuring gases become inefficient, causing a drop in response of the gas sensor. Moreover, if the number of outer-shell bottom wall openings is greater than 7, then, a probability increases for the water droplets to intrude the inside of the inner shell. This results in not only a drop in advantage of the present invention but also a decrease in a flow speed of the measuring gas stream with a resultant droop in response of the gas sensor.

With the gas sensor of the present embodiment, the plurality of outer-shell bottom wall openings are formed on the outer-shell bottom wall in a circular area outside an intersecting circle between extended lines extending along the tapered portion of the leading end portion of the inner shell and the outer-shell bottom wall.

With the outer-shell bottom wall openings formed in such a circular area, the outer-shell bottom wall openings are located in areas on extensions of the measuring gas stream passing along a tapered surface of the leading end portion of the inner-shell. This makes it easy for the water droplets in measuring gases to be expelled from the outer-shell bottom wall openings. Accordingly, the concentration sensing element is less susceptible to water-incursion.

With the gas sensor of the present embodiment, each of the outer-shell bottom wall openings may be preferably formed in a circle shape with a diameter of a value equal to or greater than 1.0 mm and equal to or less than to 2.0 mm.

With the outer-shell bottom wall openings formed in such diameters, the gas sensor has an optimum response, while allowing the concentration sensing element to have increased water-incursion resistance.

If the outer-shell bottom wall openings have diameters less than 1.0 mm, then, the exhaust gas stream is hard to be admitted through the outer-shell sidewall openings and expelled through the outer-shell bottom wall openings, resulting in a drop in response of the gas sensor.

In contrast, if the outer-shell bottom wall openings have diameters greater than 2.0 mm, then, the water droplets contained in measuring gases easily intrude the inside of the inner shell, causing a drop in the advantage of the present invention.

With the gas sensor of the present embodiment, the outer-shell bottom wall openings may be preferably formed on the outer-shell bottom wall in line with a circle concentric with an axis of the outer shell and having a diameter equal to or greater than 6.0 mm and equal to or less than to 7.0 mm.

With such a structure, the gas sensor can have an optimum response, while permitting the concentration sensing element to be less susceptible water-incursion.

If the outer-shell bottom wall openings are located inside the circular area less than 6.0 mm in diameter, the inner-shell bottom wall opening and the outer-shell bottom wall openings are brought into direct fluid communication with each other with a resultant difficulty in obtaining the advantage of the present invention.

Further, if the placement position is located outside the circle with the diameter of 7.0 mm, then, the outer shell needs to have an increased diameter and various design modification is necessitated.

With the gas sensor of the present embodiment, the bottom clearance between the outer-shell bottom wall and the inner-shell bottom wall may preferably lay in a value equal to or greater than 1.0 mm and equal to or less than 3.0 mm.

With such a structure, the gas sensor can have an optimum response, while permitting the concentration sensing element to be less susceptible water-incursion.

If the bottom clearance is less than 1.0 mm, the introduction and expelling of measuring gases become inefficient, causing a drop in response of the gas sensor.

On the contrary, if the bottom clearance is greater than 2.0 mm, then, the water droplets easily intrude the inside of the inner shell at an increased rate. This results in a drop in advantage of the present invention.

Another aspect of the present invention provides a method of operating a gas sensor to detect a concentration of a specified gas component in measuring gases flowing through a measuring gas flow passage, the method comprising preparing a concentration sensing element having a base end portion and a leading end portion for detecting the concentration of the specified gas component in the measuring gases. A housing is prepared for insertion of the concentration sensing element to fixedly support the concentration sensing element to allow the leading end portion of the concentration sensing element in a flow passage through which a stream of measuring gases flows. A bottomed cylindrical cover body structure is prepared for covering the leading end portion of the concentration sensing element and includes an outer shell, having a plurality of outer-shell sidewall openings and a plurality of outer-shell bottom wall openings, and an inner shell having a plurality of inner-shell sidewall openings, formed in areas axially dislocated from the outer-shell sidewall openings toward a bottom wall of the inner shell and opening to an upper inside area of the inner shell, and a tapered leading end portion, radially spaced from an inner periphery of the outer shell with a given amount of sideways clearance varying in a radial space along an axis of the inner shell, which has an inner-shell bottom wall axially spaced from an outer-shell bottom wall with a given amount of bottom clearance and formed with an inner-shell bottom wall opening. A measuring gas stream is admitted through the outer-shell sidewall openings to an inside of the outer shell to allow the measuring gas stream to impinge against an outer wall of the inner shell. The measuring gas stream is directed axially downward toward the bottom wall of the outer shell through the sideways clearance. A portion of the measuring gas stream is permitted to flow to the upper inside area of the inner shell through the inner-shell sidewall openings at areas downstream of the outer-shell sidewall openings. The rest of the measuring gas stream is expelled along an outer periphery of the tapered leading end portion of the inner shell through the sideways clearance and the outer-shell bottom wall openings to the measuring gas flow passage. The portion of measuring gas stream, admitted to the inner shell, is expelled through the inner-shell bottom wall opening and the outer-shell bottom wall openings to the measuring gas flow passage.

Thus, according to the present invention, the gas sensor can have a structure with increased response and increased water-incursion resistance of a concentration sensing element. In addition, the gas sensor operating method of the present invention achieves reliable operation of the gas sensor with high durability while having increased water-incursion resistance and increased response.

DETAILED DESCRIPTION OF PREFERRED EMBODIMENTS

Now, gas sensors of various embodiments according to the present invention and a related method of operating the gas sensor will be described below in detail with reference to the accompanying drawings. However, the present invention is construed not to be limited to such an embodiment described below and technical concepts of the present invention may be implemented in combination with other known technologies or the other technology having functions equivalent to such known technologies.

In the following description, it is construed that a portion of the gas sensor adapted to be inserted to a measuring gas flow passage is referred to as a "leading end portion" and an opposite side of the gas sensor exposed to an atmosphere is referred to as a "base end" or a "base end portion".

Also, it will be appreciated that the gas sensor of the present embodiment according to the present invention may have a wide variety of applications to an oxygen sensor, an A/F sensor, a NOx sensor, etc.

First Embodiment

A gas sensor of a first embodiment according to the present invention is described below in detail with reference to FIGS. 1 and 2.

Figure 1:
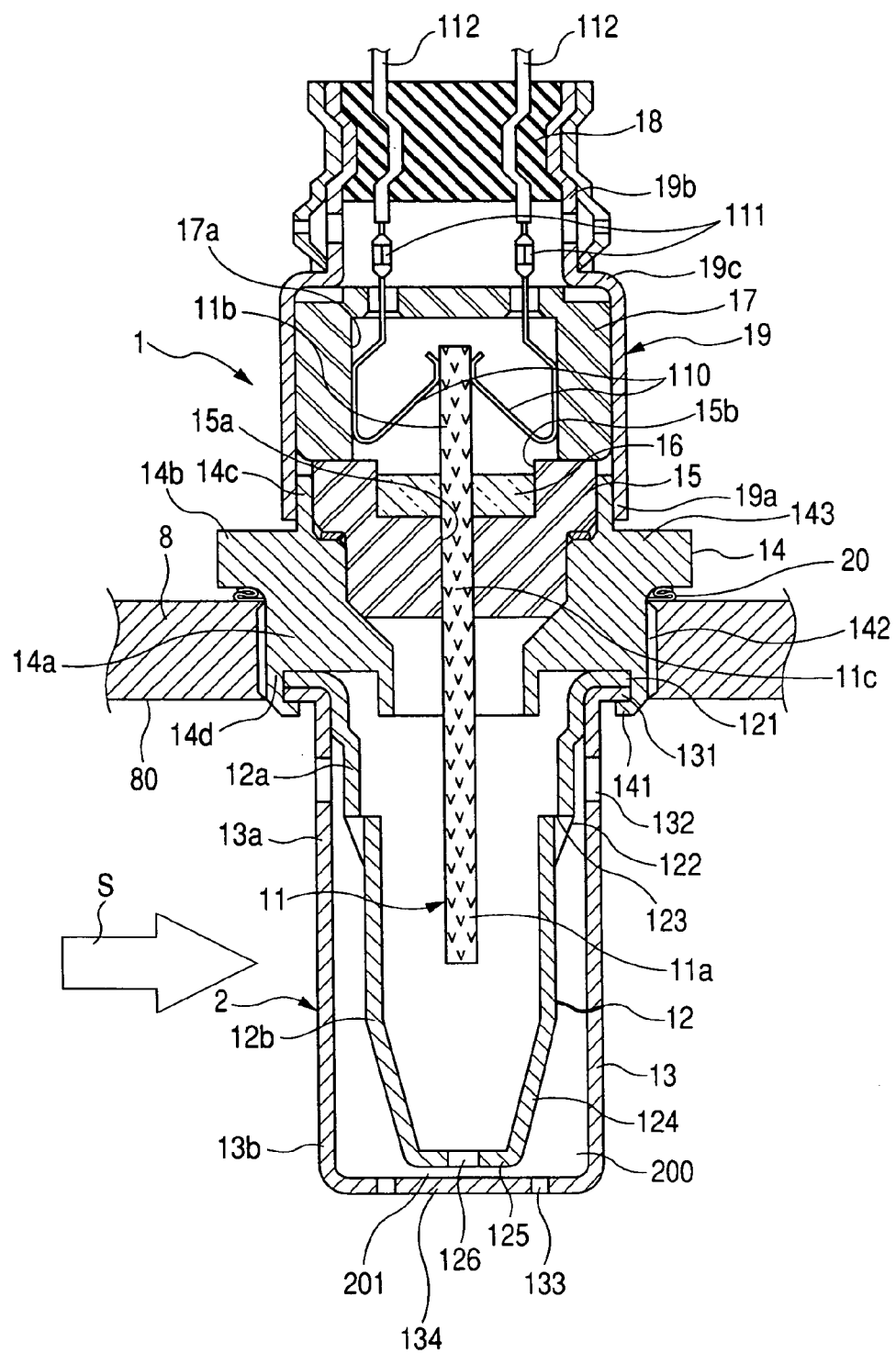
FIG. 1 is a longitudinal cross sectional view showing a gas sensor of a first embodiment according to the present invention.

As shown in FIG. 1, the gas sensor 1 comprises a gas sensing element 11 for detecting a concentration of a specified gas component in measuring gases, a housing 14 for fixedly supporting the gas sensing element 11 to be exposed to a measuring gas flow passage 80, and a cover body 2 made of, for instance, stainless steel or the like for covering the housing 14 and a leading end portion 11a of the gas sensing element 11 to be exposed to measuring gases.

The housing 14 includes a housing body 14a whose outer periphery is formed with a tool-fitting portion 14b in the form of a housing nut portion 143 with which a tool (not shown) is engageable, an upper cylindrical portion 14c axially extending upward from the housing body 14a, and a lower cylindrical portion 14d extending downward from the housing body 4a. The tool-fitting portion 14b is formed in a substantially hexagonal profile with two facing surfaces of hexagonal surfaces being distanced from each other by a given value.

As shown in FIG. 1, further, the lower cylindrical portion 14d of the housing body 14a has an outer periphery formed with a threaded portion 142 that can be screwed into a wall of, for instance, an exhaust pipe 8 of an internal combustion engine. The exhaust pipe 8 serves as the measuring gas flow passage 80. With the housing 14 mounted on the exhaust pipe 8, the leading end portion 11a of the gas sensing element 11 is exposed to a measuring gas stream S passing across the exhaust pipe 8 and a base end portion 11b of the gas sensing element 11 is exposed to an atmospheric condition.

The cover body 2 takes the form of a multi-layer structure, formed in a bottomed cylindrical shape, which includes an inner shell 12 and an outer shell 13, different from each other in diameter, which are disposed in concentric relation to each other.

The inner shell 12 takes the form of a so-called hat type that has a cylindrical shape in cross section with an opened upper end and a bottomed lower end. The upper end of the inner shell 12 has a radially extending inner-shell annular flange portion 121 that extends radially outward.

Likewise, the outer shell 13 also takes the form of a so-called hat type that has a cylindrical shape in cross section with an opened upper end and a bottomed lower end. The upper end of the outer shell 13 has a radially extending outer-shell annular flange portion 131 that extends radially outward.

The inner shell 12 and the outer shell 13 are stacked on each other such that the inner-shell annular flange portion 121 and the outer-shell annular flange portion 131 are stacked on each other. Under such a stacked state, the inner-shell annular flange portion 121 and the outer-shell annular flange portion 131 are fixedly secured to a lower end face of the housing 14 by a caulked portion 141 formed on an extreme end of the lower cylindrical portion 14d.

Figure 2A:
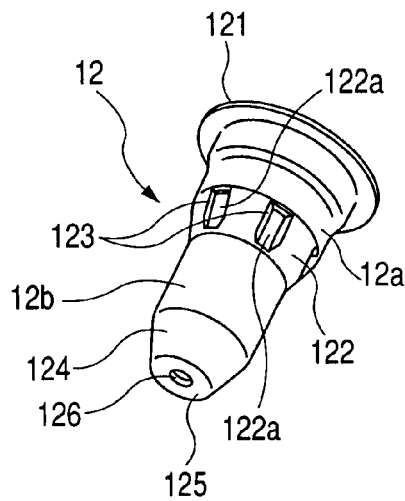
FIG. 2A is a perspective view showing a structure of an inner shell forming part of the gas sensor shown in FIG. 1.
Figure 2B:
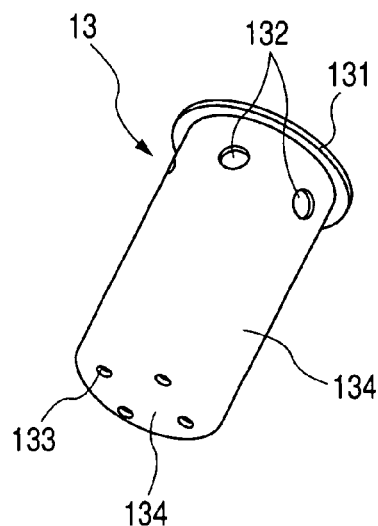
FIG. 2B is a perspective view showing a structure of an outer shell forming part of the gas sensor shown in FIG. 1.
Figure 2C:
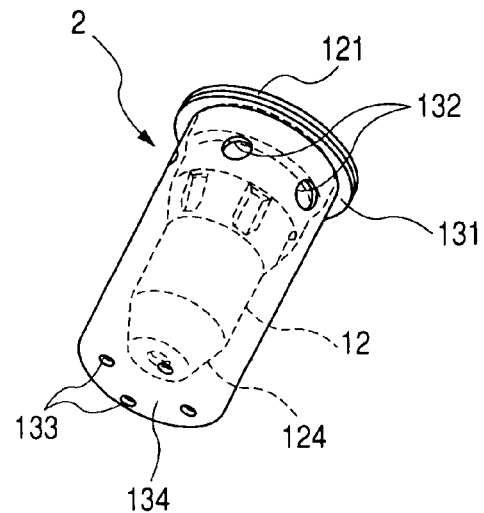
FIG. 2C is a perspective view showing a cover body structure employed in the gas sensor shown in FIG. 1.

Reference is now made to FIGS. 2A to 2C for describing structures of the inner shell 12 and the outer shell 13 forming the cover body 2 more in detail.

FIG. 2A is a perspective view showing the inner shell 12 and FIG. 2B is a perspective view showing the outer shell 13.

FIG. 2C is a perspective view showing the cover body 2 with the inner shell 12 and the outer shell 13 arranged in a combined state.

The outer shell 13 includes a base end portion 13a, acting as a cylindrical sidewall and having six outer-shell sidewall openings 132 formed at equidistantly spaced positions along a circumferential direction of the outer shell 13, and a leading end portion 13b having an outer-shell bottom wall 134. The outer-shell sidewall openings 132 are circular in cross section and each has a diameter of, for instance, 3.0 mm for admitting a stream of measuring gases to an annular sideways clearance 200 defined between the inner and outer shells 12, 13.

The outer-shell bottom wall 134 of the outer shell 13 has four outer-shell bottom wall openings 133 formed at circumferentially and equidistantly spaced positions on a circle with a diameter of 7.0 mm in a concentric relation to an axis of the outer shell 13. The outer-shell bottom wall openings 133 are circular in cross section and each has a diameter of, for instance, 1.0 mm.

As shown in FIGS. 1 and 2A, the inner shell 12 includes a base end portion 12a with an opened formed with the annular flange 121, a leading end portion 12b axially extending downward from the base end portion 12b and having the lowermost end formed with an inner-shell bottom wall 125, and an annular tapered shoulder 122 formed between the base end portion 12a and the leading end portion 12b so as to decrease in diameter toward the leading end portion 12b.

The inner-shell bottom wall 125 of the inner shell 12 has a central area formed with an inner-shell bottom wall opening 126 with a diameter of, for instance, 3.0 mm for expelling measuring gases from an inside of the inner shell 12 to an outside thereof.

The annular tapered shoulder 122 of the inner shell 12 has a plurality of inner-shell sidewall openings 123 formed in a position axially dislocated from the outer-shell sidewall openings 132 toward the leading end portion 12b at equidistantly spaced positions along a circumferential direction of the inner shell 12.

As best shown in FIG. 2A, the inner-shell sidewall openings 123 are opened toward an upper and inside area of the leading end portion 12b of the inner shell 12 so as to have opening components to allow only measuring gases to flow axially upward toward the upper and inside area of the leading end portion 12b while reliably avoiding water droplets, contained in measuring gases admitted to the inside of the outer shell 13, from intruding the upper and inside area of the leading end portion 12b.

More particularly, a plurality of radially inward depressed portions 122a may be formed on the tapered shoulder 122 of the inner shell 12 at equidistantly spaced positions along a circumferential direction of the tapered shoulder 122 by press forming so as to longitudinally extend in parallel to an axis of the inner shell 12. During such press forming operation, upper distal ends of the radially inward depressed portions 122a are formed in slit shapes, respectively, which are opened toward the upper and inside area of the base end portion 12a of the inner shell 12 as the inner-shell sidewall openings 123.

As shown in FIGS. 1 and 2A, the leading end portion 12b of the inner shell 12 has a tapered portion 124 that decreases in diameter toward the inner-shell bottom wall 125 of the inner shell 12.

Accordingly, the annular sideways clearance 200, defined between the inner and outer shells 12, 13, gradually expands in annular space toward the leading end portion 13b of the outer shell 13.

With the inner and outer shells 12, 13 stacked on each other in a concentrically assembled state as shown in FIG. 2C, an intervening bottom clearance 201 is defined between the inner-shell bottom wall 125 of the inner shell 12 and the outer-shell bottom wall 134 of the outer shell 13.

The base end portion 11b of the gas sensing element 11 is electrically connected to internal signal wire leads 110, which are connected through connecting terminals 111 to outer signal wire leads 112.

Further, the gas sensing element 11 has an intermediate portion 11c extending through a through-bore 15a of a porcelain insulating body 15. The porcelain insulating body 15 has an outer periphery accommodated in the housing body 14a and the upper cylindrical portion 14c of the housing 14. Further, the porcelain insulating body 15 has a base end portion formed with a cylindrical cavity 15b that is berried with a sealant member 16 to support the gas sensing element 11 in a fixed place in concentric relation to the housing 14 and the cover body 2.

In addition, a cup-shaped porcelain insulating member 17 is placed on the porcelain insulating body 15 at an upper end wall thereof and has a cavity 17a that covers the signal wire leads 110. Moreover, the signal wire leads 112 are embedded in an insulating member 18 and held in fixed place.

The insulating members 17, 18 are covered with an atmospheric-side cover member 19. The atmospheric-side cover member 19 has a leading end portion 19a, fixedly secured to the upper cylindrical portion 14c of the housing 14 by welding, and a base end portion 19b formed with a radially extending annular shoulder 19c. The radially extending annular shoulder 19c is held in pressured contact with an upper end face of the insulating member 19 to be forced against the insulating body 15 such that the insulating body 15 is held in pressured contact with the housing 14 in fixed place.

With the gas sensor 1 assembled in such a structure, the housing 14 is installed on the wall of the measuring gas flow passage 80 by screwing the threaded portion 142 of the housing 14 to the wall of the measuring gas flow passage 80. In this moment, the housing 14 is tightened to the wall of the measuring gas flow passage 80 so as to allow the leading end portion 11a of the gas sensing element 11, covered with the inner and outer shells 12, 13, to be exposed to the measuring gas flow stream S.

At the end of tightening operation of the housing nut portion 143, a resilient member 20 is compressed between the housing nut portion 143 of the housing 14 and an outer wall of the measuring gas flow passage 80, thereby providing a gastight sealing effect therebetween.

The gas sensing element 11 comprises a laminated type oxygen sensor element that includes an oxygen-ion conductive solid electrolyte body, made of, for instance, zirconium or the like, and a stack of a measuring electrode, a reference electrode, a reference gas introducing layer and a heating layer formed on both sides of the solid electrolyte body. In addition, the gas sensing element 11 may be utilized as a NOx censor and an air-fuel sensor, etc., which are suitably selected depending on a kind of measuring gases and a purpose of a particular control to be performed.

Figure 3A:
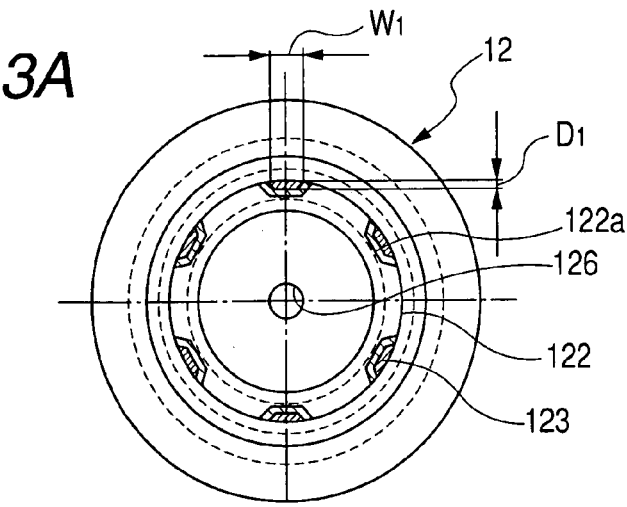
FIG. 3A is a transverse cross sectional view of a gas sensor implementing the present invention for use in an evaluation test.
Figure 3B:
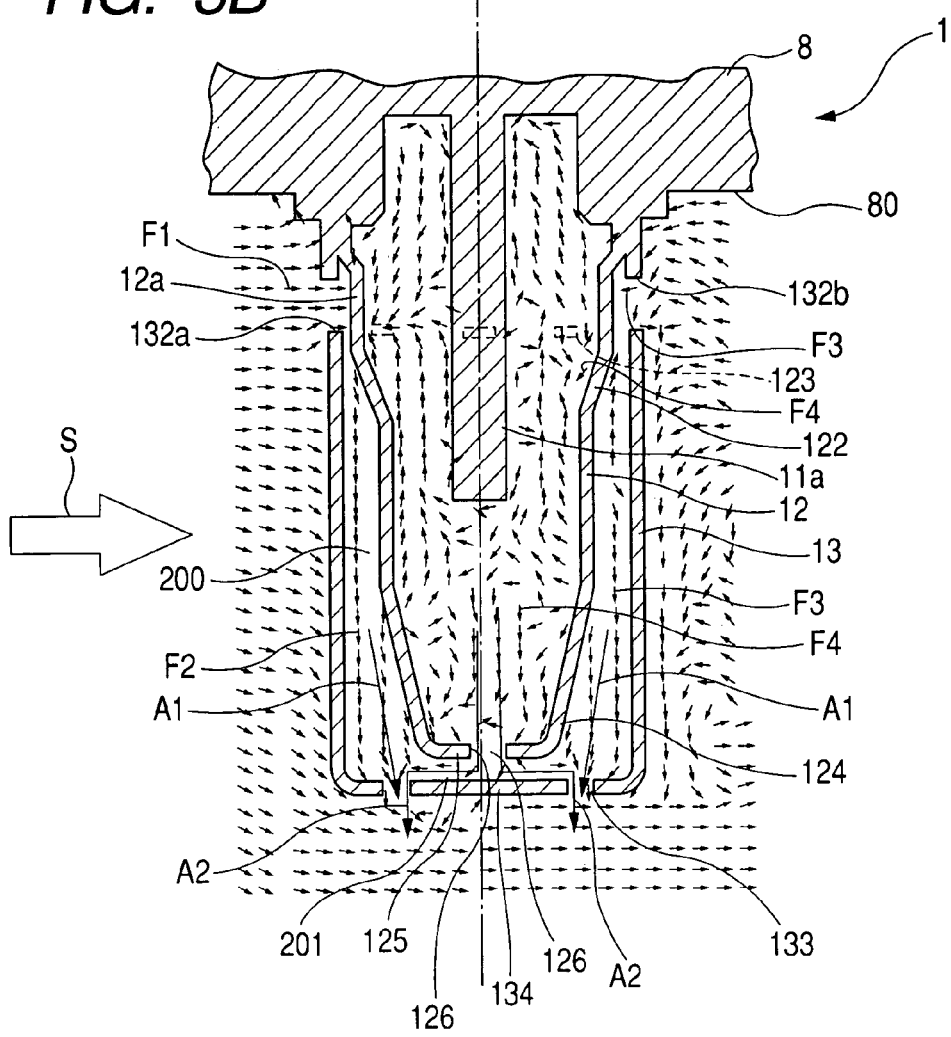
FIG. 3B is a typical view showing flow patterns of measuring gases with the gas sensor, shown in FIG. 3A, installed in a measuring gas flow passage.

FIG. 3A is a bottom view showing the inner shell 12 with associated dimensional relationships and FIG. 3B is a pattern diagram showing gas-flow velocity vectors of measuring gases passing through an area in the vicinity of the gas sensor 1.

As shown in FIG. 3A, each depressed portion 122a of the tapered shoulder 122 of the inner shell 12 is formed on the tapered shoulder 122 of the inner shell 12 to have a laterally extending slit 123 with a circumferential width $W_1$ of 2 mm and a radial depth $D_1$ of 0.5 mm.

The gas sensor 1 of the present embodiment having such an inner shell 12 was mounted on the wall 8 to be exposed to a measuring gas stream S passing through the measuring gas flow passage 80. The measuring gas stream S was set to flow at a flow rate of 25 m/sec equivalent to a flow rate of exhaust gases of an engine operating under a rotating speed of 2000 rpm.

FIG. 3B shows flow velocity vectors of measuring gases passing across an area in the vicinity of the gas sensor 1 and flowing through the inside of the gas sensor 1 when the gas sensor 1 is exposed to the measuring gas stream S flowing through the measuring gas flow passage 80 at the flow rate of 25 m/sec equivalent to the flow rate of exhaust gases expelled from the engine operating under the rotating speed of 2000 rpm.

As will be apparent from FIG. 3B, the measuring gas stream S impinges upon an outer periphery of the outer shell 13 of the gas sensor 1. In this moment, a measuring gas flow component F1 passes through an upstream-side outer-shell sidewall opening 132a, placed in the measuring gas stream S at an upstream side thereof, and impinges against an outer periphery of the base end portion 12a of the inner shell 12. This causes the measuring gas flow component F1 to deflect axially downward to form a measuring gas flow component F2 that flows into the annular sideways clearance 200 between the inner shell 12 and the outer shell 13. The measuring gas flow component F2 flows through the annular sideways clearance 200 toward the outer-shell bottom wall 134, from which the measuring gas flow component F2 is expelled through the outer-shell bottom wall openings 133 to the outside thereof as shown by arrows A1.

Due to a particular structure of the annular sideways clearance 200 expanding in an annular space toward the outer-shell bottom wall 134 between the inner and outer shells 12, 13 in the presence of the tapered portion 124, there occurs a reduction in flow-resistance of the measuring gas flow component F2. Thus, the measuring gas flow component F2 flows through the annular sideways clearance 200 at an increased flow-rate from an upstream area near the tapered shoulder 122 of the inner shell 12 toward the outer-shell bottom wall 134 of the outer shell 13.

Further, due to the measuring gas flow component F2 flowing through an area over the outer-shell bottom wall 134, measuring gases prevailing over the outer-shell bottom wall 134 are dragged through the outer-shell bottom wall openings 133 to the outside thereof as shown by arrows A2 in FIG. 3B. Thus, the measuring gas flow component is expelled from the inside of the outer shell 13 to the outside thereof in a dominant flow.

Accordingly, no water droplets intrude from the outer-shell bottom wall openings 133 of the outer shell 13 into the inside of the inner shell 12.

Further, a vortex flow occurs in the measuring gas stream S at an area downstream of the gas sensor 1. This causes a back-flow component F3 to occur in the measuring gas stream S. The back-flow component F3 is admitted through a downstream-side outer-shell sidewall opening 132b placed in the measuring gas stream S at the downstream side thereof. The back-flow component F3 is then deflected by the outer periphery of the base end portion 12a of the inner shell 12 to be directed axially downward into the sideways clearance 200.

Thereafter, the back-flow component F3, passing across the sideways clearance 200, flows into a lower end area thereof near the outer-shell bottom wall 134 of the outer shell 13, from which the back-flow component F3 is expelled through the outer-shell bottom wall openings 133 to the outside of the outer shell 13 as shown by the arrows A2.

During the flows of the measuring gas flow components F2 and F3 passing through the outer-shell bottom wall openings 133 of the outer shell 13, the measuring gas flow components F2 and F3 flow over the outer-shell bottom wall 134. This causes a negative pressure to be created in the intervening bottom clearance 201 between the inner-shell bottom wall 125 and the outer-shell bottom wall 134. Therefore, measuring gases prevailing in an area in the vicinity of the inner-shell bottom wall opening 126 to be dragged into the intervening bottom clearance 201. This causes measuring gases to be expelled through the outer-shell bottom wall openings 133 to the outside of the outer shell 13 into the measuring gas flow stream S.

During the flows of the measuring gas flow components F2 and F3 passing through the intervening bottom clearance 201 between the inner-shell bottom wall 125 and the outer shell bottom wall 134, the measuring gas flow components F2 and F3 admitted through the outer-shell sidewall openings 132a and 132b are partly admitted through the inner-shell sidewall openings 123, formed in the tapered shoulder 122 of the inner shell 12, as a measuring gas flow component F4 into the inside of the inner shell 12.

Accordingly, the measuring gas stream F4, admitted to the inside of the inner shell 12, is brought into contact with the leading end portion 11a of the gas sensing element 11 for detection of a concentration of a specified gas component in measuring gases. Then, the measuring gas flow component F4, admitted to the inside of the inner shell 12, is expelled through the inner-shell bottom wall opening 126 in the presence of the negative pressure prevailing in the intervening bottom clearance 201. Thus, the measuring gas flow component F4 is expelled through the outer-shell bottom wall openings 133 of the outer shell 13 into the measuring gas flow passage. This results in an increased response of the gas sensor 1.

Figure 4A:
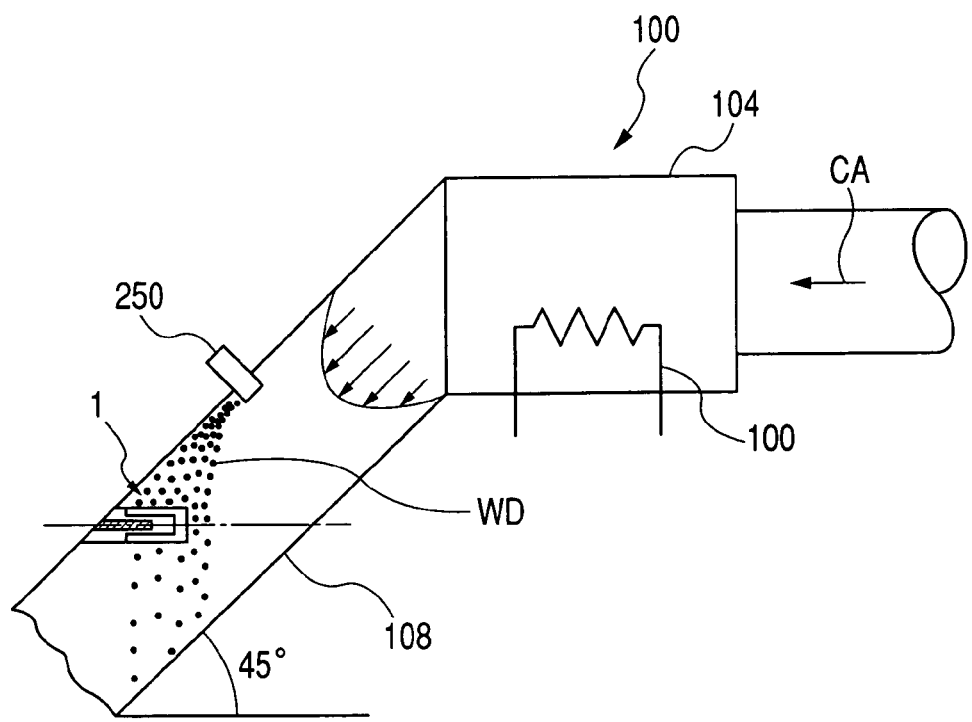
FIG. 4A is a schematic view showing a water-incursion testing device used for simulating a water-incursion pattern appearing on the gas sensor implementing the present invention.
Figure 4B:
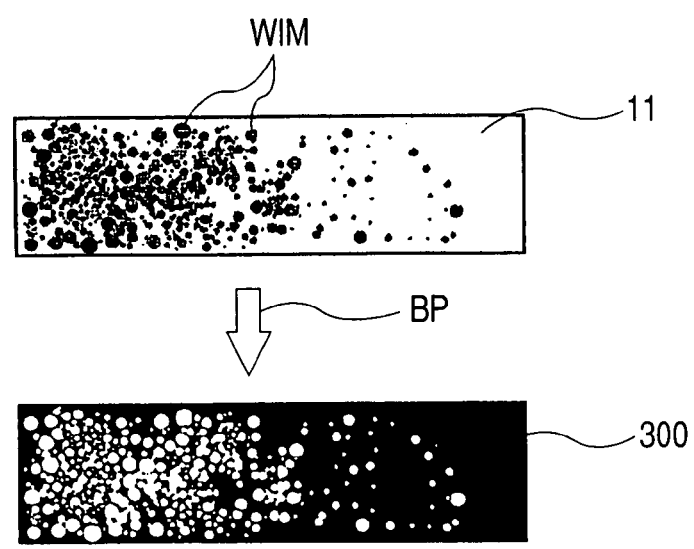
FIG. 4B is a view showing a process of evaluating a water-incursion resistance in evaluating a test result conducted using the testing device shown in FIG. 4A.

FIGS. 4A and 4B show a test method for confirming a result of the gas sensor 1 of the present embodiment. FIG. 4A shows a water-incursion resistance testing apparatus 100 for simulating the result of the gas sensor 1 of the present embodiment and FIG. 4B shows a method of evaluating a test result of the gas sensor 1 conducted in the testing apparatus shown in FIG. 4A.

As shown in FIG. 4A, the water-incursion resistance testing apparatus 100 includes a compressed air duct 102, connected to a compressed air supply (not shown) and supplied with a compressed air stream CA flowing at a flow speed of 12.6 m/sec, a heating chamber 104 communicating with the compressed air duct 102 and incorporating therein a heater 106 for heating the compressed air stream CA, and an inclined heated-air duct 108 inclined at an angle of 45° with respect to a horizontal plane, that is, an axis of the heating chamber 104. A water pump 250 is installed on the inclined heated-air duct 108 in an area immediately downstream of the heating chamber 104 to eject water droplets WD toward the gas sensor 1 into the inclined heated-air duct 108, mounted on the inclined heated-air duct 108 in area downstream the water pump 250, in five shots each with 0.2 cc.

With the water-incursion resistance testing apparatus 100 of such a structure shown in FIG. 4B, the compressed air stream CA is introduced to the heating chamber 104 at the flow speed of 12.6 m/sec and heated with the heater 106. The heated air stream is then delivered to the heated-air duct 108 used to resemble the exhaust gas pipe 8 shown in FIG. 1. When this takes place, the water droplets WD are injected to a target of the gas sensor 1 from the water pump 250 in five shots each with 0.2 cc in volume. The water droplets WD intrude through the outer-shell sidewall openings 132 or the outer-shell bottom wall openings 133 to the inside of the gas sensor 1 to adhere onto the leading end portion 11a of the gas sensing element 11.

Thereafter, the gas sensor 1 is dismounted and removed from the heated-air duct 108 and, then, disassembled to expose the gas sensing element. A photograph was taken on water-incursion marks WIM of the gas sensing element 11 resulting from the water droplets WD. Then, the water-incursion marks WIM were subjected to binary processing operation as indicated by an arrow BP to obtain binary processed data 300 as shown in FIG. 4B. This data is input to a microcomputer for calculating a water-droplet adhesion surface area to evaluate a water-incursion resistance result of the gas sensor 1.

With the water-incursion resistance testing apparatus 100 shown in FIG. 4A, the gas sensor 1 was set in an orientation at an angle of 45° with respect to the heated-air duct 108 to allow the gas sensor 1 to be susceptible to the water droplets WD.

Figure 12:
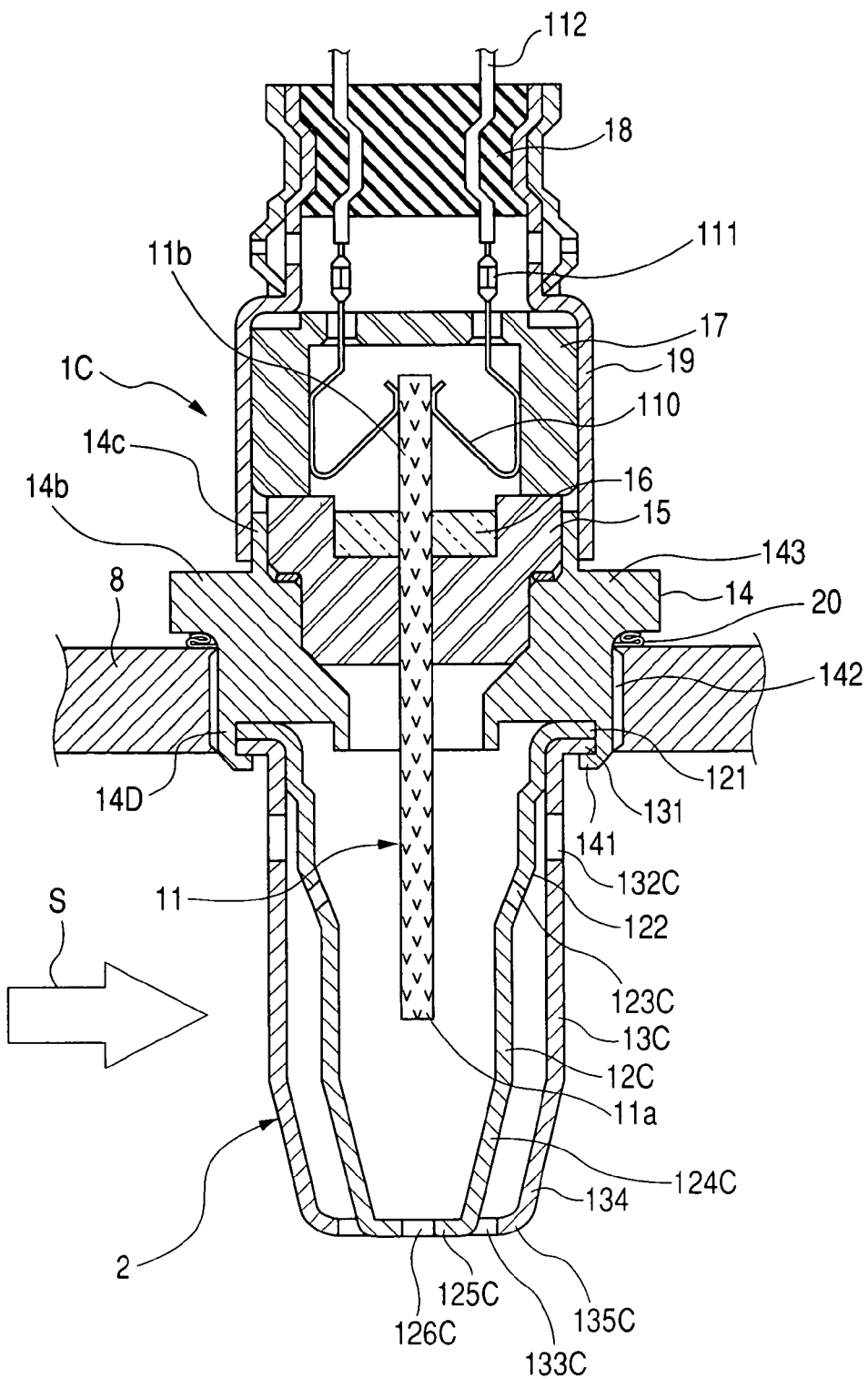
FIG. 12 is a longitudinal cross sectional view showing a structure of a gas sensor of the related art for comparison purpose.

The gas sensor 1b shown in FIG. 12 was employed as a comparison example. The same component parts of the gas sensor 1b, shown in FIG. 12, as those of the gas sensor 1 of the present embodiment shown in FIG. 1 bear like reference numerals to omit redundant description on the same component parts.

With a structure of the comparison example shown in FIG. 12, an inner-shell bottom wall 125 and an outer-shell bottom wall 135 are aligned on the same plane, under which an outer-shell bottom wall opening 133b is formed on the outer-shell bottom wall 135 in an area concentric to an inner-shell bottom wall opening 126 formed on an inner shell 12.

Figure 5:
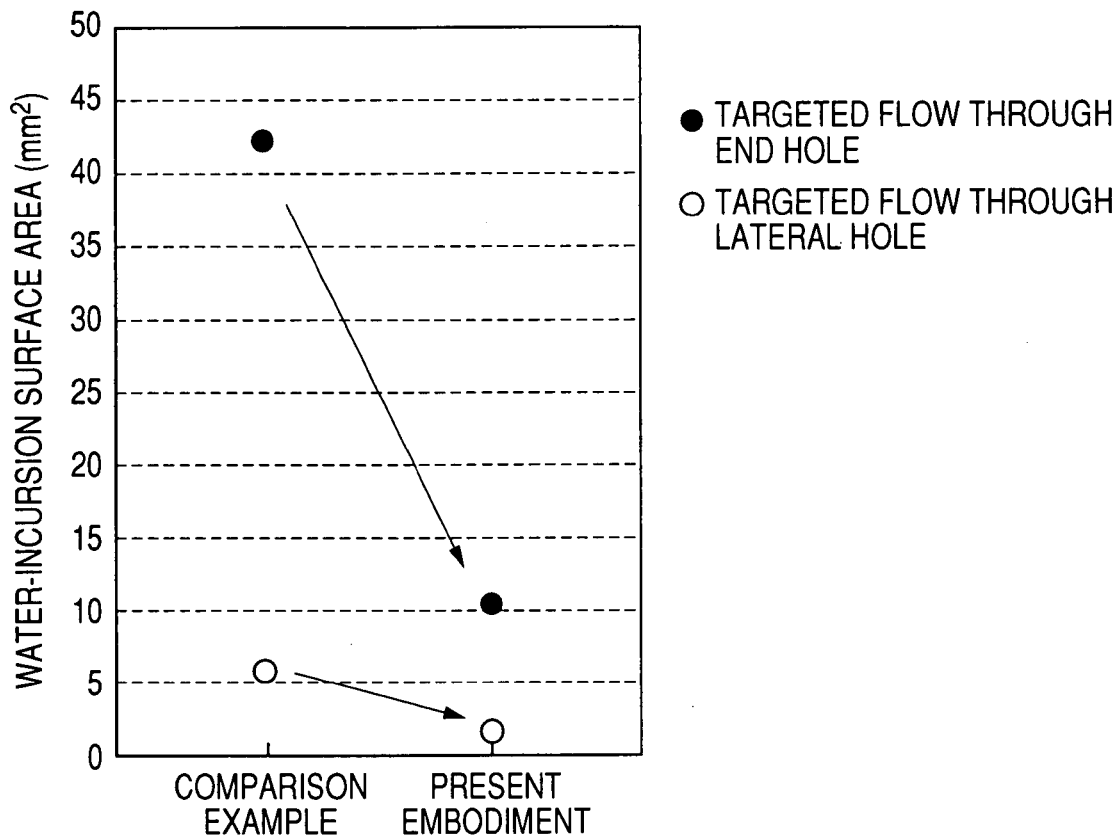
FIG. 5 is a graph showing water-incursion evaluation results of a gas sensor of the related art and the gas sensor of the present embodiment shown in FIG. 1.

FIG. 5 is a graph representing a comparison result in water-incursion surface areas subjected to water droplets between the gas sensor of the related art and the gas sensor of the first embodiment. In the graph of FIG. 5, a symbol "○": "TARGETED FLOW THROUGH LATERAL HOLE" represents a water-incursion surface area subjected to the water droplets incoming through the outer-shell sidewall opening 132. A symbol "•": "TARGETED FLOW THROUGH END HOLE" represents a water-incursion surface area subjected to the water droplets incoming through the outer-shell bottom wall opening 133.

As shown in the graph of FIG. 5, with the gas sensor of the comparison example, the gas sensing element had the water-incursion surface area in a range of approximately 40 mm$^2$ under a circumstance where the water droplets entered through the outer-shell bottom wall opening 133. On the contrary, with the gas sensor of the first embodiment implementing the present invention, the gas sensing element had the water-incursion surface area in a range of approximately 10 mm$^2$ under a circumstance where the water droplets entered through the outer-shell bottom wall opening 133. Thus, a remarkable drop occurs in value of the water-incursion surface area of the gas sensing element of the gas sensor of the first embodiment even in contrast to that of the gas sensing element of the related art when the water-droplets penetrated through the outer-shell bottom wall opening 133.

Further, with the gas sensor of the comparison example, the gas sensing element had the water-incursion surface area in a range of approximately 6 mm$^2$ under a circumstance where the water droplets entered through the outer-shell sidewall opening 132. On the contrary, with the gas sensor of the first embodiment implementing the present invention, the gas sensing element had the water-incursion surface area in a range of approximately 2 mm$^2$ under a circumstance where the water droplets entered through the outer-shell sidewall opening 132. Thus, a remarkable drop occurs in value of the water-incursion surface area of the gas sensing element of the gas sensor of the first embodiment in contrast to that of the gas sensing element of the related art even when the water-droplets penetrated through the outer-shell sidewall opening 132.

Thus, it is demonstrated that the gas sensor of the first embodiment implementing the present invention has a further increase in water-incursion resistance than that of the gas sensor of the related art.

Further, step-response tests were conducted on the gas sensor of the first embodiment implementing the present invention and the gas sensor of the related art under test conditions where both the gas sensors were mounted on an exhaust gas passage of a 3 L 6-cylinder type direct fuel-injection engine operating at an engine speed of 2000 rpm. The gas sensor of the related art had the same structure as that disclosed in FIG. 12. During the step-response tests, the engine was operating with an air-fuel ratio varied between values of "14" and "15" with 63% rate time change being measured. Thus, the step-response tests were conducted and relevant test results are shown in a graph of FIG. 6.

Figure 6:
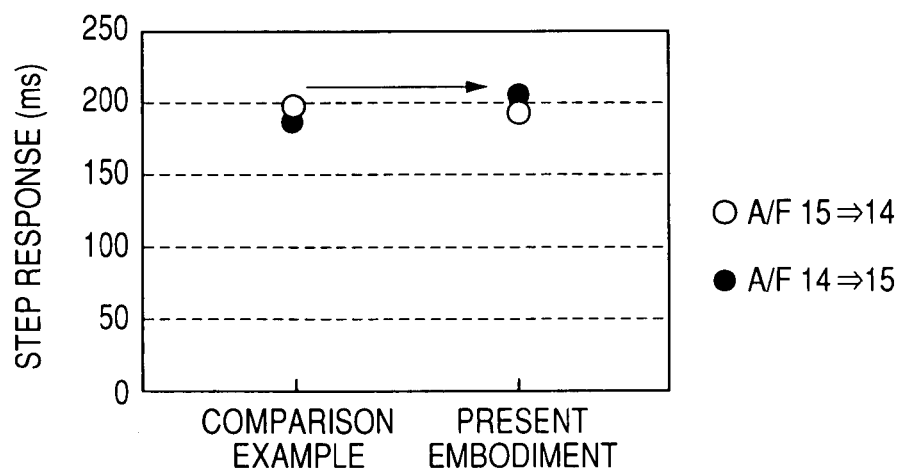
FIG. 6 is a graph showing step response evaluation results of the gas sensor of the related art and the gas sensor of the present embodiment shown in FIG. 1 under conditions where the step response tests were conducted in evaluating times changes in 63% with an air-fuel ratio shifted between 14 and 15.

FIG. 6 shows a graph representing variations in step response (millisecond) of the gas sensor of the first embodiment implementing the present invention and the gas sensor of the related art on step response evaluation tests.

In the graph of FIG. 6, symbols "○" represent the variation in step response of the gas sensors when the evaluation tests were conducted with the air-fuel ratio changed from "15" to "14". Symbols "•" represent the variation in step response of the gas sensors when the evaluation tests were conducted with the air-fuel ratio changed from "14" to "15".

As will be understood from the graph of FIG. 6, almost no difference exists in step responses of the gas sensor of the first embodiment implementing the present invention and the gas sensor of the related art even in the presence of the variation in the air-fuel ratio. Thus, it is demonstrated that the gas sensor of the first embodiment has the same response as that of the gas sensor of the related art.

Figure 7A:
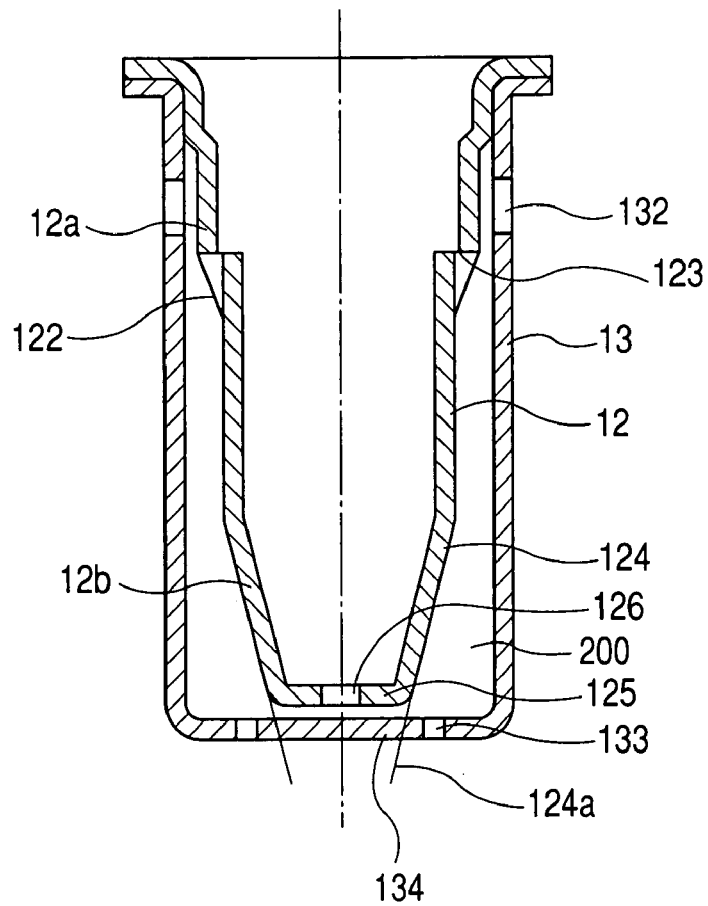
FIGS. 7A and 7B are views showing the positional relationship between a tapered surface of an inner shell and outer-shell bottom wall openings of the cover body structure employed in the gas sensor of the first embodiment shown in FIG. 1.
Figure 7B:
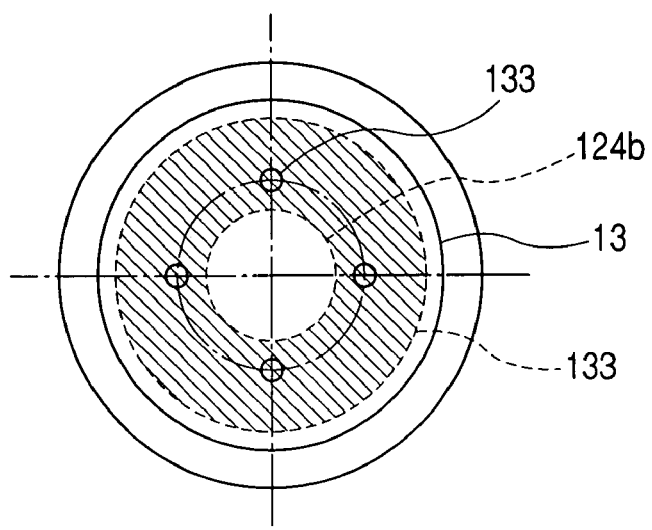

FIG. 7A is a longitudinal cross sectional view showing the inner shell 12 and the outer shell 13 in an assembled condition in an enlarged scale and FIG. 7B is a transverse cross sectional view showing the inner shell 12 and the outer shell 13 in an enlarged scale.

As shown in FIGS. 7A and 7B, suppose the tapered portion 124 of the leading end portion 12b of the inner shell 12 has extended lines 124a extending from an outer periphery of the tapered portion 124, the extended lines 124a intersect the outer-shell bottom wall 134 to form an intersecting circle 124b as shown in FIG. 7B. The outer-shell bottom wall openings 133 are formed on the bottom wall 134 of the outer shell 13 at circumferentially and equidistantly spaced positions in areas radially outward of the intersecting circle 124b. With the outer-shell bottom wall openings 133 formed in such positions, the outer-shell bottom wall openings 133 assume positions on extended lines on which measuring gases flow along a tapered surface of the leading end portion 12b. This makes it easy for the water droplets in measuring gases to escape through the outer-shell bottom wall openings 133. Accordingly, with the structure of the outer shell 13 having the outer-shell bottom wall openings 133 formed in a proper range, indicated in a hatched area in FIG. 7B, outside the intersecting circle 124b, the gas sensing element has less water-incursion.

FIGS. 8A to 8H show cover assemblies in structures with the outer shells formed with three to six bottom wall openings.

Figure 8A:
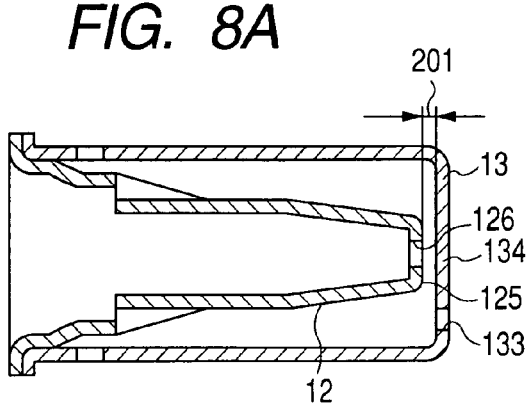
FIGS. 8A and 8B are views showing a cover body structure with an outer shell formed with three bottom wall openings.
Figure 8B:
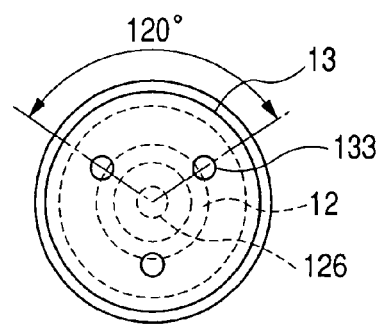

FIG. 8A is a longitudinal cross sectional view showing a structure of the outer shell 13, having three bottom wall openings 133 formed at equidistantly spaced positions on a concentric circle, and FIG. 8B is a bottom view of the outer shell 13 shown in FIG. 8A. In FIG. 8A, a reference numeral "201" represents a clearance in a bottom area (hereinafter also referred to as "bottom clearance") between the bottom walls of the inner and outer shells 12, 13.

Figure 8C:
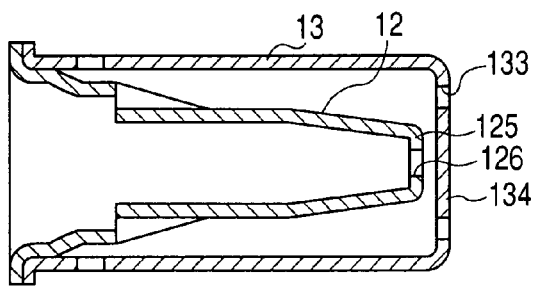
FIGS. 8C and 8D are views showing a cover body structure with an outer shell formed with four bottom wall openings.
Figure 8D:
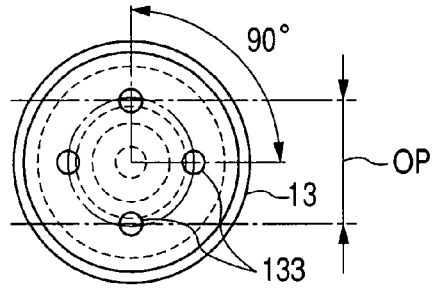

FIG. 8C is a longitudinal cross sectional view showing a structure of the outer shell 13, having four bottom wall openings 133 formed at equidistantly spaced positions on a concentric circle, and FIG. 8D is a bottom view of the outer shell 13 shown in FIG. 8C. In FIG. 8D, reference "OP" represents an opening position in which the outer-shell bottom wall openings 133 are formed.

Figure 8E:
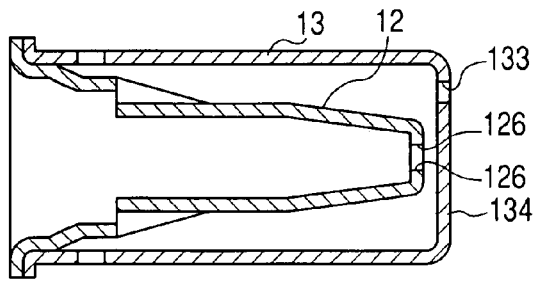
FIGS. 8E and 8F are views showing a cover body structure with an outer shell formed with five bottom wall openings.
Figure 8F:
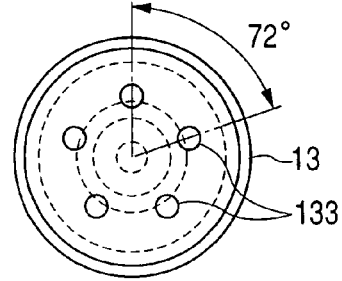

FIG. 8E is a longitudinal cross sectional view showing a structure of the outer shell 13, having fifth bottom wall openings 133 formed at equidistantly spaced positions on a concentric circle, and FIG. 8F is a bottom view of the outer shell 13 shown in FIG. 8E.

Figure 8G:
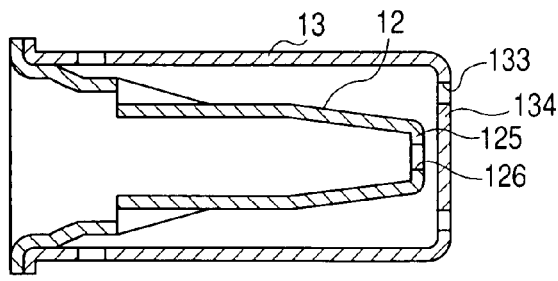
FIGS. 8G and 8H are views showing a cover body structure with an outer shell formed with six bottom wall openings.
Figure 8H:
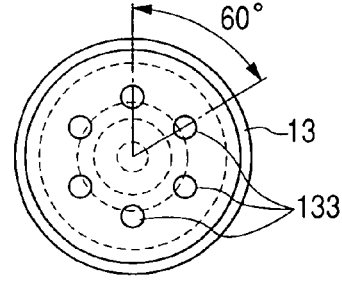

FIG. 8G is a longitudinal cross sectional view showing a structure of the outer shell 13, having six bottom wall openings 133 formed at equidistantly spaced positions on a concentric circle, and FIG. 8H is a bottom view of the outer shell 13 shown in FIG. 8G.

Figure 9:
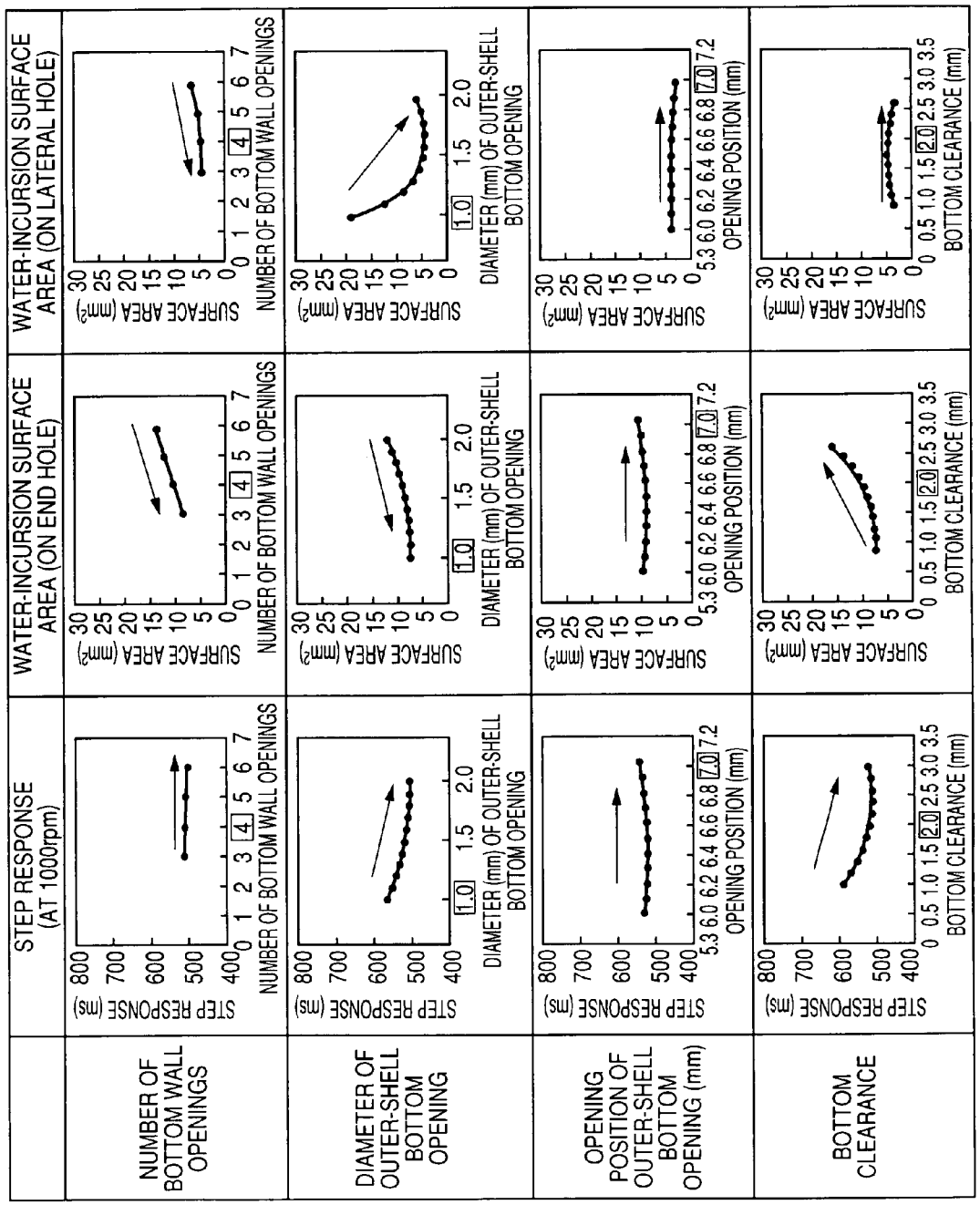
FIG. 9 is a view showing graphs plotting advantageous effects of the present invention appearing on gas sensors implemented in various modes.

FIG. 9 shows test results on response and water-incursion surface area of gas sensors of various embodiments according to the present invention. However, the step response tests were conducted on the engine operating at a low engine speed, that is, a speed of 1000 rpm, where the gas sensors were subjected to a high probability in water-incursion.

In FIG. 9, a first line represents test results on gas sensors with the varying number of bottom wall openings formed in the outer shells of the gas sensors, which were tested on an engine operating at an engine speed of 1000 rpm.

In FIG. 9, a first line shows the test results plotted in first to third graphs representing variations in step responses (millisecond), water-incursion surface areas (mm$^2$) related to end holes, and water-incursion surface areas (mm$^2$) related to lateral holes of the gas sensors.

Further, a second line shows the test results, conducted for the gas sensors with varying diameters of outer-shell bottom wall openings, which are plotted in first to third graphs representing variations in step responses (millisecond), water-incursion surface areas (mm$^2$) related to end holes, and water-incursion surface areas (mm$^2$) related to lateral holes of the gas sensors.

Furthermore, a third line shows the test results, conducted for the gas sensors with varying opening positions in which the outer-shell bottom wall openings are formed, which are plotted in first to third graphs representing variations in step responses (millisecond), water-incursion surface areas (mm$^2$) related to end holes, and water-incursion surface areas (mm$^2$) related to lateral holes of the gas sensors.

Moreover, a fourth line shows the test results, conducted for the gas sensors with varying bottom clearances between the bottom walls of the inner and outer shells of the gas sensors, which are plotted in first to third graphs representing variations in step responses (millisecond), water-incursion surface areas (mm$^2$) related to end holes, and water-incursion surface areas (mm$^2$) related to lateral holes of the gas sensors.

As will be apparent from the first line of FIG. 9, almost no variation appears in step responses of the gas sensors even in cases where the number of outer-shell bottom wall openings formed in the outer shell 13 of the gas sensors were varied from "3" to "6".

The water-incursion surface area varies such that the larger the number of the outer-shell bottom wall openings, the higher will be the probability of the water-droplets incurring from the outer-shell bottom wall openings with the resultant increase the water-incursion surface area.

As will be apparent from the first line of FIG. 9, further, the water-incursion surface area influenced by the water droplets incoming through the outer-shell bottom wall openings varies such that the larger the number of the outer-shell bottom wall openings, the greater will be the water-incursion surface area even in a slight degree of an increase.

As a consequence, for the gas sensor to have increased water-incursion resistance while maintaining proper response, the number of outer-shell bottom wall openings to be provided in the gas sensor may be preferable as less as possible. However, in a case where the outer shell 13 has three bottom wall openings, the gas sensor water-incursion resistance depending on a directional characteristic resulting from the outer-shell bottom wall openings with a resultant difficulty in actual workability. Therefore, the gas sensor may preferably have four outer-shell bottom wall openings in consideration of actual workability.

The step response of the gas sensor varies such that the larger the diameter of the outer-shell bottom wall opening, the higher will be the step response of the gas sensor due to an increase in an exchange rate of measuring gases relative to the gas sensor.

However, as the diameter of the outer-shell bottom wall opening increases, there is an increase in a probability for the water droplets to intrude from the outer-shell bottom wall opening of the gas sensor with a resultant increase in a water-incursion surface area of the gas sensing element.

Meanwhile, as the diameter of the outer-shell bottom wall opening increases, the water droplets, intruded through to the inside of the inner shell, are liable to be expelled through the outer-shell bottom wall opening at a high rate. This causes a reduction in water-incursion surface area of the gas sensing element. Accordingly, the outer-shell bottom wall opening may be preferably selected to have a diameter falling in a value ranging from 11.0 mm to 2.0 mm in consideration of workability.

As set forth above, the outer-shell bottom wall openings may be preferably formed on the outer-shell bottom wall 134 in the area outside the intersecting line 124b between the extended line 124a, extending the outer surface of the tapered portion 124 of the leading end portion 12b of the inner shell 12, and the outer-shell bottom wall 134. With the outer-shell bottom wall openings formed in such a proper position, the outer-shell bottom wall openings can be placed in the areas on the extended lines in which measuring gases flow along the tapered surface of the leading end portion 12b of the inner shell 12. This allows the water droplets, prevailing in measuring gases, to easily escape through the outer-shell bottom wall openings of the gas sensor.

Meanwhile, even if the opening positions for the outer-shell bottom wall openings to be formed is varied in a value ranging from 6.0 mm to 7.0 mm, almost no variation occurs in step response and water-incursion of the gas sensor.

Accordingly, the opening position of the outer-shell bottom wall opening may be preferably selected to fall in an arbitrary value ranging from 6.0 mm to 7.0 mm. When taking manageability of workability into consideration, the outer-shell bottom wall opening may be preferably formed in a value of 7.0 mm.

It is turned out that the greater the bottom clearance 201 (see FIG. 8A) between the inner-shell bottom wall 125 and the outer-shell bottom wall 134, the higher will be the step response of the gas sensor.

However, as the bottom clearance 201 increases, no evaporation of the water droplets takes place in such an increased bottom clearance, making it easy for the water droplets to be freely movable therein. This results in an increase in water-incursion of the gas sensor.

Further, almost no adverse affect arises on the water-incursion surface area of the gas sensor due to the bottom clearance 201 under which the water droplets intrude through the outer-shell bottom wall openings of the gas sensor.

Accordingly, the bottom clearance 201 may be preferably set to lie in a range equal to or greater than 1.0 mm and equal to or less than 3.0 mm with the account for the response and water-incursion of the gas sensor and, more preferably in a range of, for instance, 2.0 mm.

Figure 10:
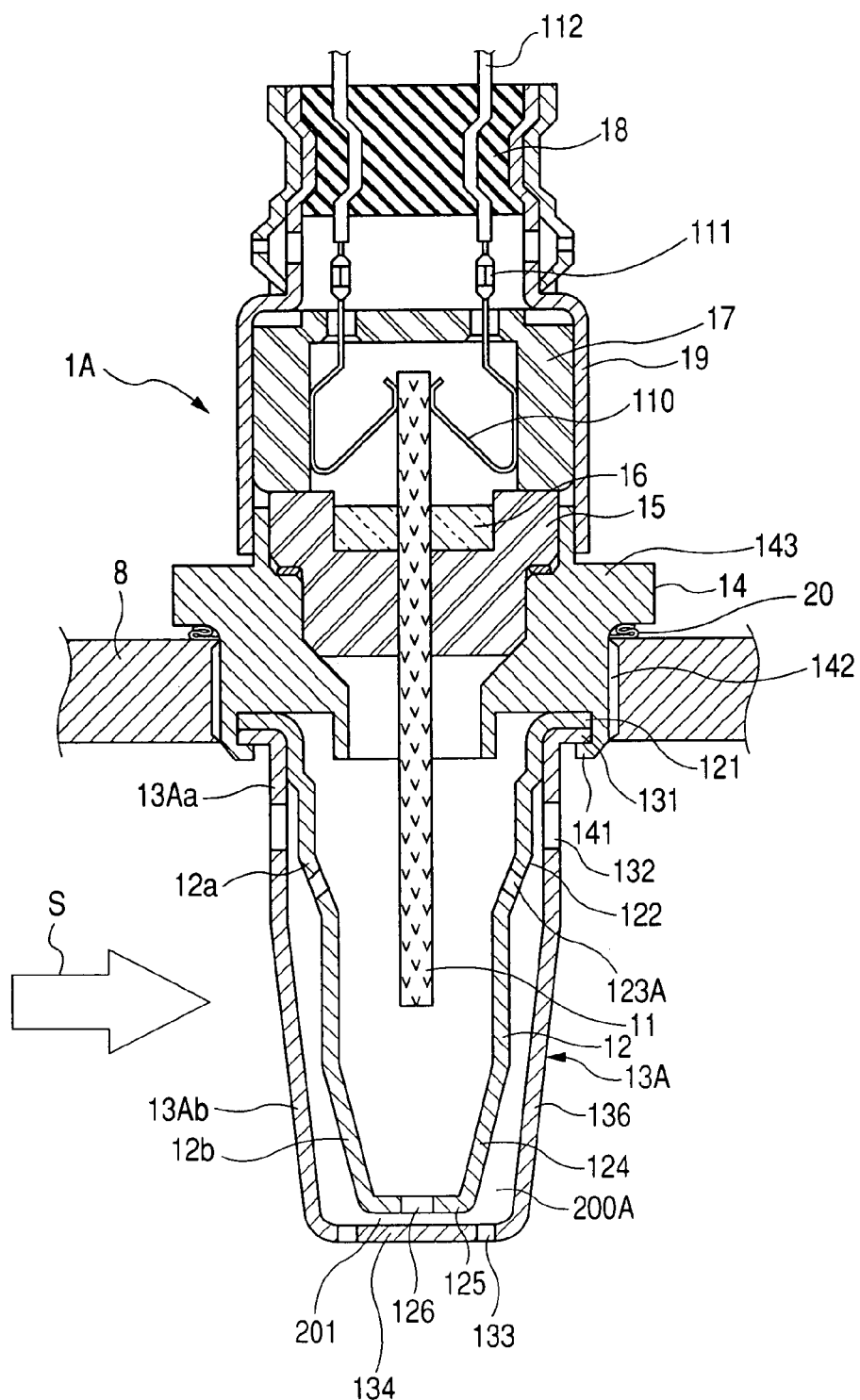
FIG. 10 is a longitudinal cross sectional view showing a gas sensor of a second embodiment according to the present invention.

FIG. 10 is a longitudinal cross sectional view showing a structure a gas sensor of a second embodiment according to the present invention.

The gas sensor of the second embodiment differs from the gas sensor of the first embodiment shown in FIG. 1 in respect of a structure of the outer shell 13. Thus, the same component parts of the gas sensor of the second embodiment as those of the gas sensor of the first embodiment bear like reference numerals to omit redundant description.

With the gas sensor 1A of the second embodiment, an outer shell 13A has a base end portion 13Aa, formed in a substantially cylindrical shape, and a tapered leading end portion 13Ab playing a role as an outer-shell tapered portion 136 that decreases in diameter toward a distal end of the outer shell 13A.

With the inner shell 12 and the outer shell 13 formed in such structures, the cover body structure of the gas sensor 1A has an annular space 200A between an outer wall of the tapered leading end 12b of the inner shell 12 and an inner wall of the tapered leading end 13Ab of the outer shell 13 that locally becomes narrow in space. This causes a stream of measuring gases, intruded to an inside of the outer shell 13A, to flow toward the bottom wall 134 of the outer shell 13A at an accelerated flow rate. This enables water droplets, prevailing in measuring gases admitted through the outer-shell sidewall openings 132, to easily escape from the outer-shell bottom wall openings 133. Therefore, the gas sensing element 11 of the gas sensor 1A of the present embodiment has increased water-incursion resistance.

Figure 11:
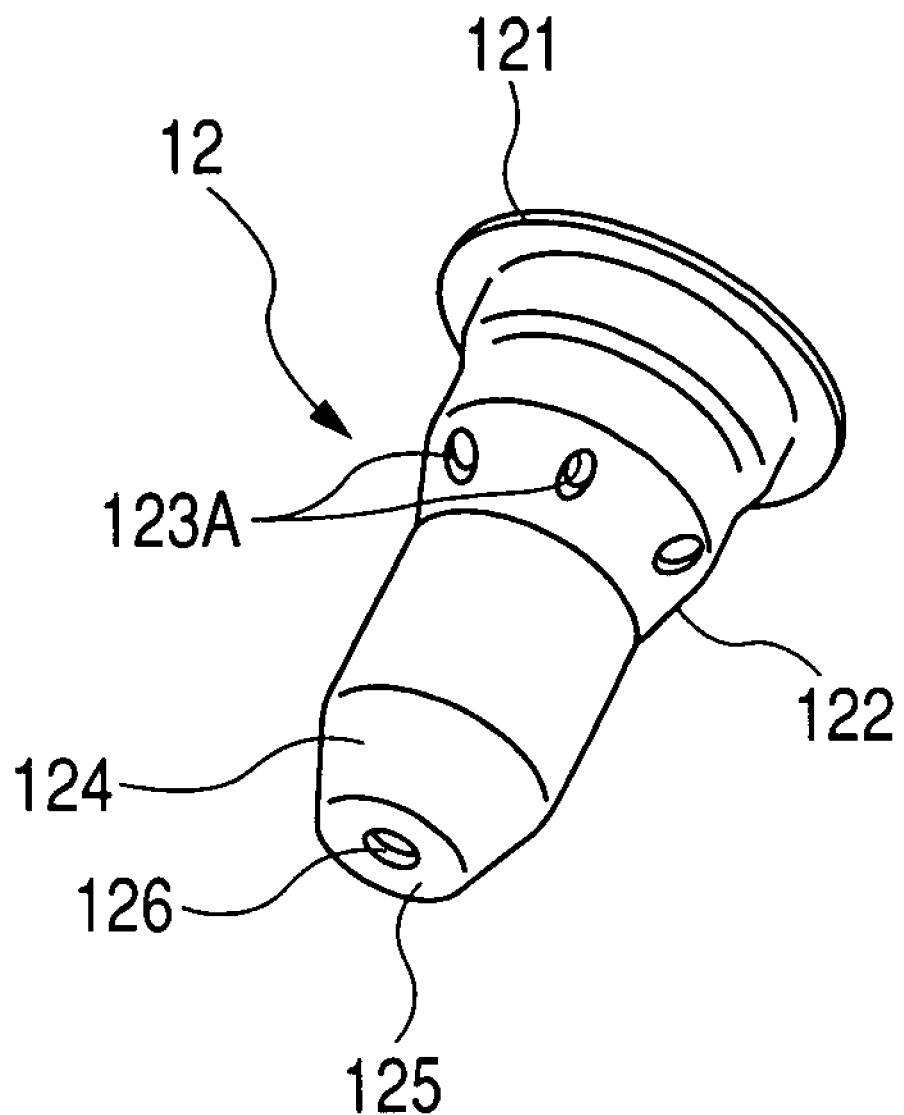
FIG. 11 is a perspective view of the inner shell showing inner-shell sidewall openings formed in a modified form.

FIG. 11 shows a modified for of the inner shell 12. While the gas sensors of the various embodiments have been described above with reference to the inner shell 12 having the sidewall openings 123 formed in the form of the plurality of slit shapes located in the concaved portion formed in the base end portion 12a of the inner shell 12, the present invention is not limited to such a structure. That is, the inner shell 12 may have the base end portion 12a formed with the tapered portion 124 that decreases in diameter toward the leading end portion 12b. With the inner shell 12 formed in such a structure, a plurality of sidewall openings 123A may be formed on the tapered portion 122 in circumferentially and equidistantly spaced positions at areas axially far from the sidewall openings 132 of the outer shell 13 toward the leading end portion 12b of the inner shell 12. In this case, the sidewall openings 123A are oriented in an upward direction to have components directed from an outside area toward an inside area. This allows only a measuring gas stream to be introduced to the inside of the inner shell 12 while avoiding the intrusion of the water droplets contained in measuring gases.

While the present invention has been described above with reference to the cover body structure in the form of the double layer structure, the present invention is not limited to such a structure. That is, the cover body structure may be formed in a triple layer structure that additionally includes an outermost cover concentrically disposed on an outside area of the outer shell 13 in a concentric relation therewith. With such a triple layer structure, the gas sensor has an increased heat-retaining property to stabilize an activated state of the gas sensing element. Therefore, the gas sensor of such a structure can have increased response in operation.

While the present invention has been described with reference to the structure including the gas sensing element of, for instance, the laminated type, the present invention may be applied to a gas sensor of a cup type.

Further, a structure of a gas sensor disclosed in Japanese Patent Application No. 2006-12407 filed by the present inventor may be suitably applied to the inner-shell sidewall openings.

While the specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention, which is to be given the full breadth of the following claims and all equivalents thereof.

What is claimed is:

1. A gas sensor for detecting a concentration of a specified gas component in measuring gases, comprising:
    a concentration sensing element having a base end portion and a leading end portion for detecting the concentration of the specified gas component in the measuring gases;
    a housing for insertion of the concentration sensing element to fixedly support the concentration sensing element to allow the leading end portion of the concentration sensing element in a flow passage through which a stream of measuring gases flows; and
    a bottomed cylindrical cover body structure, fixedly supported with the housing and having a cylindrical multiple-layer structure, which includes an inner shell and an outer shell different in diameter from each other and disposed in a concentric relation to each other so as to surround the leading end portion of the concentration sensing element in an area exposed to the stream of measuring gases;
    wherein an annular sideways clearance is defined between an outer periphery of the inner shell and an inner periphery of the outer shell;
    wherein the inner shell has a base end portion and a leading end portion, the base end portion of the inner shell having inner-shell sidewall openings formed in components directed upward from an outside area of the inner shell to an inside area thereof, the inner shell having an inner-shell bottom wall whose central area is formed with an inner-shell bottom wall opening;
    wherein the outer shell has a base end portion and a leading end portion, the base end portion of the outer shell having a plurality of outer-shell sidewall openings for admitting the stream of measuring gases to the annular sideways clearance;
    wherein the leading end portion of the outer shell has an outer-shell bottom wall spaced from the inner-shell bottom wall to define a bottom clearance therebetween;
    wherein a plurality of outer-shell bottom wall openings are formed on the outer-shell bottom wall in an outer circumferential area radially outside the inner-shell bottom wall opening;
    wherein the inner shell has a plurality of inner-shell sidewall openings axially offset from the outer-shell sidewall openings of the outer shell to positions closer to the leading end portion of the inner shell; and wherein the leading end portion of the outer shell includes a tapered portion that decreases in diameter toward the outer-shell bottom wall.

2. The gas sensor according to claim 1, wherein:
the leading end portion of the inner shell includes a tapered portion that decreases in diameter toward the inner-shell bottom wall.

3. The gas sensor according to claim 1, wherein:
the inner shell includes a tapered shoulder, formed in an area between the base end portion and the leading end portion of the inner shell, which decreases in diameter toward the inner-shell bottom wall, and a plurality of concaved portions, formed in the area between the base end portion and the leading end portion of the inner shell, wherein the inner-shell sidewall openings are formed in slit shapes in at least one of the tapered shoulder and the plurality of concaved portions.

4. The gas sensor according to claim 1, wherein:
the plurality of outer-shell bottom wall openings include three to six openings formed at equidistantly spaced positions in a circular area concentric to an axis of the outer shell.

5. The gas sensor according to claim 1, wherein:
the plurality of outer-shell bottom wall openings are formed on the outer-shell bottom wall in a circular area outside an intersecting circle between extended lines extending along the tapered portion of the leading end portion of the inner shell and the outer-shell bottom wall.

6. The gas sensor according to claim 1, wherein:
each of the outer-shell bottom wall openings is formed in a circle shape with a diameter of a value equal to or greater than 1.0 mm and equal to or less than to 2.0 mm.

7. The gas sensor according to claim 1, wherein:
the outer-shell bottom wall openings are formed on the outer-shell bottom wall in line with a circle concentric with an axis of the outer shell and having a diameter equal to or greater than 6.0 mm and equal to or less than to 7.0 mm.

8. The gas sensor according to claim 1, wherein:
the bottom clearance between the outer-shell bottom wall and the inner-shell bottom wall lies in a value equal to or greater than 1.0 mm and equal to or less than 3.0 mm.

9. The gas sensor according to claim 1, wherein:
the inner shell includes a tapered shoulder, formed in an area between the base end portion and the leading end portion of the inner shell, which decreases in diameter toward the inner-shell bottom wall; and
wherein the inner-shell sidewall openings include a plurality of concaved portions formed in slit shapes so as to open to an upper inside area of the inner shell to permit measuring gases, admitted to an inside of the outer shell, to flow upward in the upper inside area of the inner shell.

10. The gas sensor according to claim 1, wherein:
the inner shell includes a tapered shoulder, formed in an area between the base end portion and the leading end portion of the inner shell, which decreases in diameter toward the inner-shell bottom wall;
wherein the inner-shell sidewall openings include a plurality of openings formed on the tapered shoulder at equidistantly spaced positions so as to open to an upper inside area of the inner shell to permit measuring gases, admitted to an inside of the outer shell, to flow upward in the upper inside area of the inner shell.

11. The gas sensor according to claim 1, wherein:
the outer shell has a cylindrical shape in cross section;
the inner shell includes a tapered shoulder, formed in an area between the base end portion and the leading end portion of the inner shell, which decreases in diameter toward the inner-shell bottom wall; and
wherein the inner-shell sidewall openings open to an upper inside area of the inner shell to permit measuring gases, admitted to an inside of the outer shell, to flow upward in the upper inside area of the inner shell.

12. A gas sensor for detecting a concentration of a specified gas component in measuring gases, comprising:
a concentration sensing element having a base end portion and a leading end portion for detecting the concentration of the specified gas component in the measuring gases;
a housing for insertion of the concentration sensing element to fixedly support the concentration sensing element to allow the leading end portion of the concentration sensing element in a flow passage through which a stream of measuring gases flows; and
a bottomed cylindrical cover body structure, fixedly supported with the housing and having a cylindrical multiple-layer structure, which includes an inner shell and an outer shell different in diameter from each other and disposed in a concentric relation to each other so as to surround the leading end portion of the concentration sensing element in an area exposed to the stream of measuring gases;
wherein an annular sideways clearance is defined between an outer periphery of the inner shell and an inner periphery of the outer shell;
wherein the inner shell has a base end portion and a leading end portion, the base end portion of the inner shell having inner-shell sidewall openings formed in components directed upward from an outside area of the inner shell to an inside area thereof, the inner shell having an inner-shell bottom wall whose central area is formed with an inner-shell bottom wall opening;
wherein the outer shell has a base end portion and a leading end portion, the base end portion of the outer shell having a plurality of outer-shell sidewall openings for admitting the stream of measuring gases to the annular sideways clearance;
wherein the leading end portion of the outer shell has an outer-shell bottom wall spaced from the inner-shell bottom wall to define a bottom clearance therebetween;
wherein a plurality of outer-shell bottom wall openings are formed on the outer-shell bottom wall in an outer circumferential area radially outside the inner-shell bottom wall opening;
wherein the inner shell has a plurality of inner-shell sidewall openings axially offset from the outer-shell sidewall openings of the outer shell to positions closer to the leading end portion of the inner shell;
wherein the base end portion of the outer shell has a cylindrical shape in cross section and the leading end portion of the outer shell is tapered in cross section;
wherein the inner shell includes a tapered shoulder, formed in an area between the base end portion and the leading end portion of the inner shell, which decreases in diameter toward the inner-shell bottom wall; and
wherein the inner-shell sidewall openings open to an upper inside area of the inner shell to permit measuring gases, admitted to an inside of the outer shell, to flow upward in the upper inside area of the inner shell.

13. A method of operating a gas sensor to detect a concentration of a specified gas component in measuring gases flowing through a measuring gas flow passage, the method comprising:

preparing a concentration sensing element having a base end portion and a leading end portion for detecting the concentration of the specified gas component in the measuring gases;

preparing a housing for insertion of the concentration sensing element to fixedly support the concentration sensing element to allow the leading end portion of the concentration sensing element in a flow passage through which a stream of measuring gases flows; and preparing a bottomed cylindrical cover body structure for covering the leading end portion of the concentration sensing element and including an outer shell, having a plurality of outer-shell sidewall openings and a plurality of outer-shell bottom wall openings, and an inner shell having a plurality of inner-shell sidewall openings, formed in areas axially dislocated from the outer-shell sidewall openings toward a bottom wall of the inner shell and opening to an upper inside area of the inner shell, and a tapered leading end portion, radially spaced from an inner periphery of the outer shell with a given amount of sideways clearance varying in a radial space along an axis of the inner shell, which has an inner-shell bottom wall axially spaced from an outer-shell bottom wall with a given amount of bottom clearance and formed with an inner-shell bottom wall opening;

admitting a measuring gas stream through the outer-shell sidewall openings to an inside of the outer shell to allow the measuring gas stream to impinge against an outer wall of the inner shell;

directing the measuring gas stream axially downward toward the bottom wall of the outer shell through the sideways clearance;

permitting a portion of the measuring gas stream to flow to the upper inside area of the inner shell through the inner-shell sidewall openings at areas downstream of the outer-shell sidewall openings;

expelling the rest of the measuring gas stream along an outer periphery of the tapered leading end portion of the inner shell through the sideways clearance and the outer-shell bottom wall openings to the measuring gas flow passage; and expelling the portion of measuring gas stream, admitted to the inner shell, through the inner-shell bottom wall opening and the outer-shell bottom wall openings to the measuring gas flow passage.

14. A gas sensor for detecting a concentration of a specified gas component in measuring gases, comprising:

a concentration sensing element having a base end portion and a leading end portion for detecting the concentration of the specified gas component in the measuring gases;

a housing for insertion of the concentration sensing element to fixedly support the concentration sensing element to allow the leading end portion of the concentration sensing element in a flow passage through which a stream of measuring gases flows; and a bottomed cylindrical cover body structure, fixedly supported with the housing and having a cylindrical multiple-layer structure, which includes an inner shell and an outer shell different in diameter from each other and disposed in a concentric relation to each other so as to surround the leading end portion of the concentration sensing element in an area exposed to the stream of measuring gases;

wherein an annular sideways clearance is defined between an outer periphery of the inner shell and an inner periphery of the outer shell;

wherein the inner shell has a base end portion and a leading end portion, the base end portion of the inner shell having inner-shell sidewall openings formed in components directed upward from an outside area of the inner shell to an inside area thereof, the inner shell having an inner-shell bottom wall whose central area is formed with an inner-shell bottom wall opening;

wherein the outer shell has a base end portion and a leading end portion, the base end portion of the outer shell having a plurality of outer-shell sidewall openings for admitting the stream of measuring gases to the annular sideways clearance;

wherein the leading end portion of the outer shell has an outer-shell bottom wall spaced from the inner-shell bottom wall to define a bottom clearance therebetween;

wherein a plurality of outer-shell bottom wall openings are formed on the outer-shell bottom wall in an outer circumferential area radially outside the inner-shell bottom wall opening; and wherein the leading end portion of the outer shell includes a tapered portion that decreases in diameter toward the outer-shell bottom wall.

* * * * *